United States Patent
Munro

(10) Patent No.: US 7,384,905 B2
(45) Date of Patent: Jun. 10, 2008

(54) PYRIDINE DERIVATES USEFUL AS FRAGRANCE MATERIALS

(75) Inventor: David Munro, Maidstone (GB)

(73) Assignee: Quest International Services B.V., Naarden (NL)

( * ) Notice: Subject to any disclaimer, the term of this patent is extended or adjusted under 35 U.S.C. 154(b) by 601 days.

(21) Appl. No.: 10/535,832

(22) PCT Filed: Oct. 2, 2003

(86) PCT No.: PCT/GB03/04271

§ 371 (c)(1), (2), (4) Date: May 20, 2005

(87) PCT Pub. No.: WO2004/048336

PCT Pub. Date: Jun. 10, 2004

(65) Prior Publication Data

US 2006/0154851 A1 Jul. 13, 2006

(30) Foreign Application Priority Data

Nov. 22, 2002 (GB) ................................. 0227253.2

(51) Int. Cl.
*A61K 8/00* (2006.01)

(52) U.S. Cl. ........................................ 512/10; 546/348
(58) Field of Classification Search ................ 546/348; 512/10
See application file for complete search history.

(56) References Cited

U.S. PATENT DOCUMENTS 4,539,143 A 9/1985 Boden et al.

FOREIGN PATENT DOCUMENTS

DE 4029776 A1 3/1992
EP 0470391 A1 2/1992

OTHER PUBLICATIONS

H. Brunner et al., Tetrahedron: Asymmetry, vol. 9, issue 8, p. 1277, Apr. 1998. Abstract only.*
H. Brunner et al., Tetrahedron: Asymmetry, vol. 9, issue 3, pp. 407-422, Feb. 1998. Abstract only.*

* cited by examiner

*Primary Examiner*—John R Hardee
(74) *Attorney, Agent, or Firm*—Morgan, Lewis & Bockius LLP

(57) ABSTRACT

A novel compound is having the structure, Formula (I): exhibits interesting odor characteristics, generally green in nature, particularly of a tomato leaf character, and so find use in perfumes and perfumed products.

13 Claims, No Drawings

PYRIDINE DERIVATES USEFUL AS FRAGRANCE MATERIALS

FIELD OF THE INVENTION

This invention concerns novel fragrance compounds, their method of production, and their use in perfumes and perfumed products.

SUMMARY OF THE INVENTION

In one aspect the present invention provides a compound having the structure

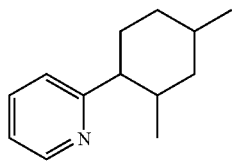

This compound is known as 2-(2,4-dimethylcyclohexyl) pyridine, but for brevity and simplicity will be referred to herein as "the pyridine", "the novel pyridine" or "the pyridine of the invention".

The pyridine of the invention can possess fragrance or odour properties which are generally regarded as interesting, pleasant or attractive.

The novel pyridine of the invention has three stereogenic i.e. chiral centres and can thus exist in a total of eight isomeric forms, more particularly as 2-[(1S,2S,4S)-2,4-dimethylcyclohexyl]pyridine, 2-[(1S,2R,4S)-2,4-dimethylcyclohexyl]pyridine, 2-[(1S,2S,4R)-2,4-dimethylcyclohexyl]pyridine, 2-[(1R,2S,4S)-2,4-dimethylcyclohexyl]pyridine, 2-[(1R,2S,4R)-2,4-dimethylcyclohexyl]pyridine, 2-[(1S,2R,4R)-2,4-dimethylcyclohexyl]pyridine, 2-[(1R,2R,4R)-2,4dimethylcyclohexyl]pyridine and 2-[(1R,2R,4S)-2,4-dimethylcyclohexyl]pyridine, and the invention includes within its scope each individual isomer and also mixtures of two or more isomers. Thus, mixtures of isomers of the pyridine of the invention are referred to in this specification in the singular, e.g. as the pyridine, so that references to the pyridine may refer to one or other isomeric form or mixtures of isomers.

Each individual isomer of the pyridine of the invention may have has its own odour properties. The odour qualities of two of the eight possible isomers of the novel pyridine have been assessed as follows:

|  | Odour (Dry) | Odour (Fresh) |
| --- | --- | --- |
| 2-[(1S,2R,4R)-2,4-dimethylcyclohexyl]pyridine | Grapefruit Rhubarb Green Metallic | Grapefruit Rhubarb Green |
| 2-[(1R,2R,4S)-2,4-dimethylcyclohexyl]pyridine | Green Tomato leaf Minty Petitgrain | Green Tomato leaf Minty |

A preferred isomer of the pyridine in accordance with the invention because of its desirable odour note which may generally be described as reminiscent of tomato-leaf, is 2-[(1R,2R,4S)-2,4-dimethylcyclohexyl]pyridine. As will be described below, this isomer is typically produced as part of a mixture with 2-[(1R,2R,4R)-2,4-dimethylcyclohexyl]pyridine.

Thus, in an even further aspect, the present invention provides the pyridine of the invention in the form of a mixture of 2-[(1R,2R,4R)-2,4-dimethylcyclohexyl]pyridine and 2-[(1R,2R,4S)-2,4-dimethylcyclohexyl]pyridine.

Such a mixture of isomers has been found to possess a wide range of chemical and olfactive stability and so finds potential use in a number of products. The mixture also has excellent radiance properties, where radiance is a measure of the ease with which the odour of one or more molecules is perceived, typically within a closed environment. Radiance is thus a function of the odour threshold and volatility of a particular molecule(s). Generally, in order to obtain the desired odour note reminiscent of tomato leaf from such a mixture, the mixture conveniently contains 2-[(1R,2R,4R)-2,4-dimethylcyclohexyl]pyridine in an amount of between 80% and 20% by weight of the total weight of the mixture, preferably between 70% and 30% by weight, more preferably about 30% by weight, and 2-[(1R,2R,4S)-2,4-dimethylcyclohexyl]pyridine in an amount of between 20% and 80% by weight of the total weight of the mixture, preferably between 30% and 70% by weight, more preferably about 70% by weight.

The odour properties of the pyridine of the invention mean that it may be used as such to impart, strengthen or improve the odour of a wide variety of products, or may be used as a component of a perfume (or fragrance composition) to contribute its odour character to the overall odour of such perfume. For the purposes of this invention a perfume is intended to mean a mixture of fragrance materials, if desired mixed with or dissolved in a suitable solvent or mixed with a solid substrate, which is used to impart a desired odour to the skin and/or product for which an agreeable odour is indispensable or desirable. Examples of such products are: fabric washing powders, washing liquids, fabric softeners and other fabric care products; detergents and household cleaning, scouring and disinfection products; air fresheners, room sprays and pomanders; soaps, bath and shower gels, shampoos, hair conditioners and other personal cleansing products; cosmetics such as creams, ointments, toilet waters, preshave, aftershave, skin and other lotions, talcum powders, body deodorants and antiperspirants, etc.

Other fragrance materials which can be advantageously combined with the pyridine of the invention in a perfume are, for example, natural products such as extracts, essential oils, absolutes, resinoids, resins, concretes, etc., but also synthetic materials such as hydrocarbons, alcohols, aldehydes, ketones, ethers, acids, esters, acetals, ketals, nitrites, etc., including saturated and unsaturated compounds, aliphatic, carbocyclic, and heterocyclic compounds.

Such fragrance materials are mentioned, for example, in S. Arctander, Perfume and Flavour Chemicals (Montclair, N.J., 1969), in S. Arctander, Perfume and Flavor Materials of Natural Origin (Elizabeth, N.J., 1960) and in "Flavor and Fragrance Materials-1991", Allured Publishing Co. Wheaton, Ill. USA.

Examples of fragrance materials which can be used in combination with the pyridine of the invention are: geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nopol, nopyl acetate, 2-phenyl-ethanol, 2-phenylethyl acetate, benzyl alcohol, benzyl acetate, benzyl salicylate, styrallyl acetate, benzyl benzoate, amyl salicylate, dimethylbenzyl-carbinol, trichloromethylphenyl-carbinyl acetate, p-tert-butylcyclohexyl acetate, isononyl acetate, vetiveryl acetate, vetiverol, α-hexylcinnamaldehyde, 2-methyl-3-(p-tert-butylphenyl)propanal, 2-methyl-3-(p-isopropylphenyl)propanal, 2-(p-tert-butylphenyl)propanal, 2,4-dimethyl-cyclohex-3-enyl-carboxaldehyde, tricyclodecenyl acetate, tricyclodecenyl propionate, 4-(4-hydroxy-4-methyl-pentyl)-3-cyclohexenecarboxyaldehyde, 4-(4-methyl-3-pentenyl)-3-cyclohexenecarboxaldehyde, 4-acetoxy-3-pentyl-tetrahydropyran, 3-carboxymethyl-2-pentylcyclopentane, 2-n-heptylcyclopentanone, 3-methyl-3-pentyl-2-cyclopentenone, n-decanal, n-dodecanal, 9-decenol-1, phenoxyethyl isobutyrate, phenylacetaldehyde dimethylacetal, phenylacetaldehyde diethylacetal, geranyl nitrile, citronellyl nitrile, cedryl acetate, 3-isocamphylcyclohexanol, cedryl methyl ether, isolongifolanone, aubepine nitrile, aubepine, heliotropin, coumarin, eugenol, vanillin, diphenyl oxide, hydroxycitronellal, ionones, methylionones, isomethylionones, irones, cis-3-hexenol and esters thereof, indan musks, tetralin musks, isochroman musks, macrocyclic ketones, macrolactone musks, ethylene brassylate.

Solvents which can be used for perfumes containing the pyridine of the invention are, for example: ethanol, isopropanol, diethyleneglycol monoethyl ether, dipropylene glycol, diethyl phthalate, triethyl citrate, isopropyl myristate, etc.

The quantities in which the pyridine according to the invention can be used in perfumes or in products to be perfumed may vary within wide limits and depend, inter alia, on the nature of the product, on the nature and the quantity of the other components of the perfume in which the pyridine is used and on the olfactive effect desired. It is therefore only possible to specify wide limits, which, however, provide sufficient information for the specialist in the art to be able to use the pyridine according to the invention for his specific purpose. Typically, a perfume comprises the pyridine of the invention in an olfactively effective amount. In perfumes, an amount of 0.01% by weight or more of the pyridine of the invention will generally have a clearly perceptible olfactive effect. Preferably the amount is 0.1 to 80% by weight, more preferably at least 1%. The amount of the pyridine according to the invention present in products will generally be at least 10 ppm by weight, preferably at least 100 ppm, more preferably at least 1000 ppm. However, levels of up to about 20% by weight may be used in particular cases, depending on the product to be perfumed.

In a further aspect the invention provides a perfume comprising the pyridine of the invention in an olfactively effective amount.

The invention also covers a perfumed product comprising the pyridine of the invention.

The pyridine of the invention, that is 2-(2,4-dimethylcyclohexyl)pyridine, may be synthesised by a Diels-Alder reaction between 2-vinylpyridine and 2-methyl-1,3-pentadiene to produce 2-(2,4-dimethylcyclohex-3-en-1-yl)pyridine, which is then subjected to a hydrogenation reaction to give 2-(2,4-dimethylcyclohexyl)pyridine. The reaction may be shown schematically as follows:

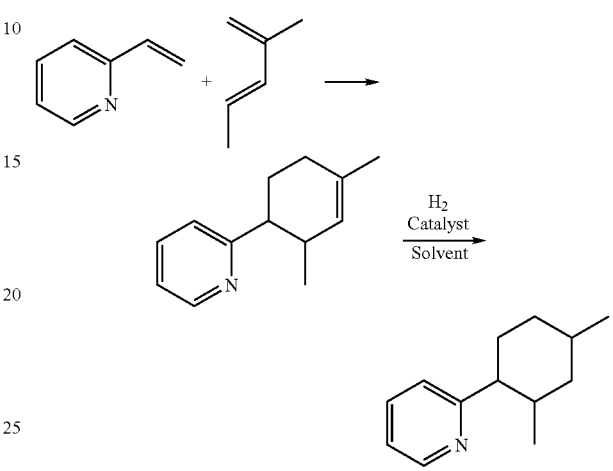

Thus, in a further aspect, the invention provides a method of making a compound in accordance with the invention, comprising reacting 2-vinylpyridine and 2-methyl-1,3-pentadiene to cause a Diels-Alder reaction to produce 2-(2,4-dimethylcyclohex-3-en-1-yl)pyridine, and subjecting 2-(2,4-dimethylcyclohex-3-en-1-yl)pyridine to a hydrogenation reaction to give 2-(2,4-dimethylcyclohexyl)pyridine.

The Diels-Alder reaction is conveniently carried out at a temperature in the range 150° C. to 200° C., preferably about 190° C. The reaction is also typically carried out under pressure, e.g. in the range 3 bar to 6 bar, preferably about 5 bar, to give 2-(2,4-dimethylcyclohex-3-en-1-yl)pyridine as a mixture of isomers typically comprising as the predominant isomers of the mixture, the diastereoisomers, 2-[(1R,2R)-2,4-dimethylcyclohex-3-en-1-yl]pyridine and 2-[(1R,2S)-2,4-dimethylcyclohex-3-en-1-yl]pyridine as follows:

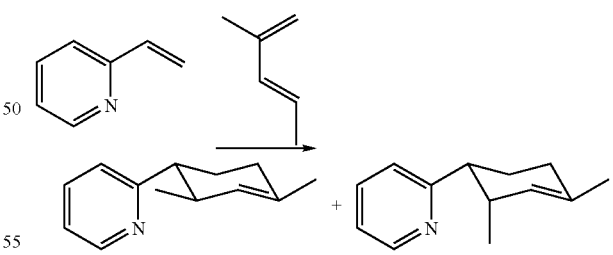

These isomers are typically formed in approximately equal amounts.

The hydrogenation reaction may be performed either on the mixture of isomers of 2-(2,4-dimethylcyclohex-3-en-1-yl)pyridine, or on an individual isomer which may be separated from the mixture, e.g. by column chromatography (silica; hexane 85%: methyl tertiary-butyl ether (herein after 'MTBE') 15%).

The hydrogenation reaction is typically carried out in the presence of a hydrogenation catalyst, e.g. palladium supported on carbon or Raney nickel, in a solvent such as ethanol. The reaction may be conveniently performed at a temperature of about 80° C. and a pressure of about 5 bar for a time of about 2 hours, and generally results in the production of a mixture of isomers of the pyridine of the invention, as follows:

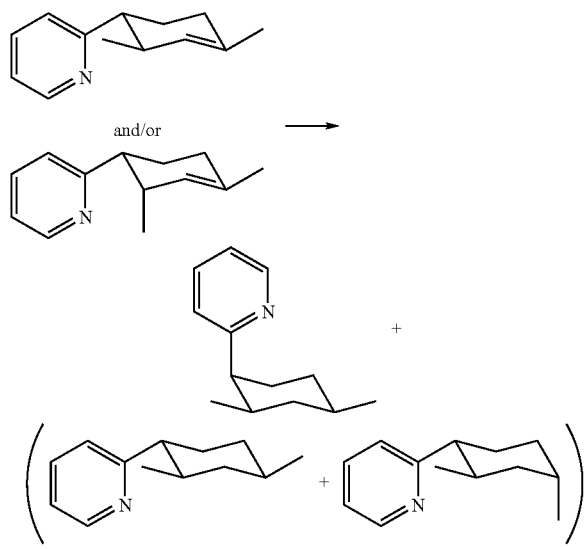

Typically, this mixture of isomers is separated using known separation techniques such as chromatography. For example, 2-[(1S,2R,4R)-2,4-dimethylcyclohexyl]pyridine can be isolated by column chromatography as a single isomer (e.g. by GLC 100% rpa), whilst 2-[(1R,2R,4R)-2,4-dimethylcyclohexyl]pyridine and 2-[(1R,2R,4S)-2,4-dimethylcyclohexyl]pyridine are generally obtained a mixture.

The relative amounts of each individual isomer is dependent on the precise conditions used for their formation and whether the hydrogenation reaction is carried out on the mixture of isomers of 2-(2,4-dimethylcyclohex-3-en-1-yl) pyridine or an individual isomer thereof. For example, it has been found that when the hydrogenation reaction is performed on 2-[(1R,2S)-2,4-dimethylcyclohex-3-en-1-yl]pyridine, the major product formed in the resulting mixture of isomers of the pyridine of the invention is 2-[(1S,2R,4R)-2,4-dimethylcyclohexyl]pyridine. By contrast, hydrogenation of 2-[(1R,2R)-2,4-dimethylcyclohex-3-en-1-yl]pyridine conveniently gives a mixture of the 2-[(1R,2R,4R)-2,4-dimethylcyclohexyl]pyridine and 2-[(1R,2R,4S)-2,4-dimethylcyclohexyl]pyridine isomers as the major reaction product.

Good results in terms of reproducibility and selectivity for the preferred 2-[(1R,2R,4S)-2,4-dimethylcyclohexyl]pyridine have been obtained by carrying out a hydrogenation reaction, e.g. on 2-[(1R,2R)-2,4-dimethylcyclohex-3-en-1-yl]pyridine using Raney nickel as the hydrogenation catalyst. Thus, the currently preferred hydrogenation catalyst is Raney nickel.

In a further aspect, the present invention provides a method of making the pyridine of the invention in the form of a mixture of 2-[(1R,2R,4R)-2,4-dimethylcyclohexyl]pyridine and 2-[(1R,2R,4S)-2,4-dimethylcyclohexyl]pyridine comprising reacting 2-vinylpyridine and 2-methyl-1,3-pentadiene to cause a Diels-Alder reaction to produce a mixture of isomers of 2-(2,4-dimethylcyclohex-3-en-1-yl)pyridine, separating the isomer 2-[(1R,2R)-2,4-dimethylcyclohex-3-en-1-yl]pyridine from the mixture, and subjecting it to a hydrogenation reaction as a one stage process which is carried out using Raney nickel as the hydrogenation catalyst to give a mixture of isomers of 2-(2,4-dimethylcyclohexyl) pyridine, and isolating therefrom 2-[(1R,2R,4R)-2,4-dimethylcyclohexyl]pyridine and 2-[(1R,2R,4S)-2,4-dimethylcyclohexyl]pyridine as a mixture.

However, it has been observed by the present inventors that when Raney nickel is employed as the catalyst, the hydrogenation reaction may, before reaction completion, begin to over-run, e.g. reducing the pyridine ring to produce a piperidine by-product. For this reason, it may be advantageous to perform the hydrogenation reaction in two stages. Stage 1 may be performed using Raney nickel as the hydrogenation catalyst and stopping the reaction when it begins to over-reduce. Reaction progress may be conveniently monitored by a person of ordinary skill using known techniques, e.g. GLC. Stage 2 may then be carried out using 5% palladium supported on carbon (Pd/C) as the hydrogenation catalyst to drive the reaction to completion. It may be necessary to separate the reaction products of stage 1, e.g. by silica column chromatography, before the second stage hydrogenation reaction is carried out so as to remove any piperidine by-product.

In an even further aspect, the present invention provides a method of making the pyridine of the invention in the form of a mixture of 2-[(1R,2R,4R)-2,4-dimethylcyclohexyl]pyridine and 2-[(1R,2R,4S)-2,4-dimethylcyclohexyl]pyridine, comprising reacting 2-vinylpyridine and 2-methyl-1,3-pentadiene to cause a Diels-Alder reaction to produce a mixture of isomers of 2-(2,4-dimethylcyclohex-3-en-1-yl)pyridine, separating the isomer 2-[(1R,2R)-2,4-dimethylcyclohex-3-en-1-yl]pyridine from the mixture, and subjecting it to a hydrogenation reaction which is carried out as a two stage process to give a mixture of isomers of 2-(2,4-dimethylcyclohexyl)pyridine, and isolating therefrom 2-[(1R,2R,4R)-2,4-dimethylcyclohexyl]pyridine and 2-[(1R,2R,4S)-2,4dimethylcyclohexyl]pyridine as a mixture.

Preferably, the two stage hydrogenation reaction is carried out using Raney nickel for the first stage hydrogenation and palladium supported on carbon for the second stage hydrogenation.

The invention will be further described, by way of illustration, in the following Examples, where Kovats indices are assigned by GLC to each isomer produced in a reaction mixture. A discussion of Kovats indices and their significance may be found in WO 99/18926, incorporated herein by reference.

GC/GLC conditions used for analyses in the following examples:

| | |
|---|---|
| Instrument: | Hewlett Packard HP 6890 Gas Chromatograph |
| Column: | SE54 capillary column |
| Temperature Programme: | 100° C. (initial oven temperature), ramp at 12° C./min to 250° C. |
| Carrier Gas: | Hydrogen |
| Solvent/Injection Volume: | Acetone/0.1 µl |

EXAMPLE 1

This example describes synthesis of 2-(2,4-dimethylcyclohex-3-en-1-yl)pyridine by the following Diels-Alder reaction:

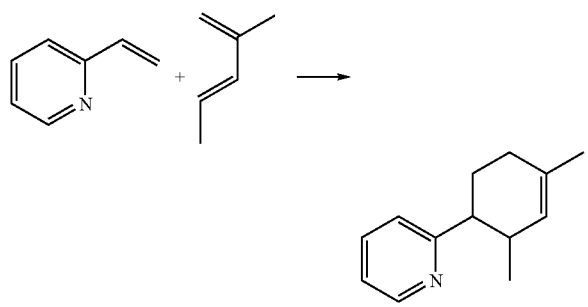

2-vinylpyridine (200 g, 1.9 mol) and 2-methyl-1,3-pentadiene (200 g, 2.4 mol) were charged to a 1 litre Buchi autoclave and then heated together to 190° C. at a pressure of 5 bar for 3 hours with stirring. After cooling, the reaction mixture was then distilled under vacuum using a 25.4 cm (10 inch) Vigreux column. After a short fore-run, b.p. 85° C./0.5 mbar, 2-(2,4-dimethylcyclohex-3-en-1-yl) pyridine (44.9%) was obtained as a mixture of isomers as shown below. Kovats 1472, 1485, 1494 and 1511.

|  | Fraction 2 (72 g) b.p. 100° C./ 0.3 mbar | Fraction 3 (74 g) b.p. 100° C./ 0.3 mbar | Fraction 4 (14 g) b.p. 100° C./ 0.3 mbar |
| --- | --- | --- | --- |
| KOVATS 1472 | 52.1% | 47.3% | 36.8% |
| KOVATS 1485 | 4.3% | 4.8% | 4.8% |
| KOVATS 1494 | 4.2% | 5.2% | 5.8% |
| KOVATS 1511 | 32.7% | 41.1% | 47.9% |

Fractions 3 and 4 were combined. Purification by chromatography (silica; hexane 90%: MTBE 10%) gave, firstly, a colourless oil (30.2 g) which was identified as 2-[(1R,2R)-2,4-dimethylcyclohex-3-en-1-yl]pyridine. Further elution gave a mixture of 2-[(1R,2R)-2,4-dimethylcyclohex-3-en-1-yl]pyridine and 2-[(1R,2S)-2,4-dimethylcyclohex-3-en-1-yl]pyridine (19.7 g), followed by 2-[(1R,2S)-2,4-dimethylcyclohex-3-en-1-yl]pyridine (27.1 g).

2-[(1R,2R)-2,4-dimethylcyclohex-3-en-1-yl]pyridine (Kovats 1472)

$^1$H NMR (CDCl$_3$, 400 MHz) δppm: 8.44 (d,6-pyridyl), 7.42 (dd,4-pyridyl), 6.95 (d,3-pyridyl), 6.90 (dd,5-pyridyl), 5.15 (d,$\underline{C}$H=C—CH$_3$), 2.40 (m,2-cyclohexyl), 2.30 (ddd, 1-cyclohexyl), 2.0-1.85(m,5,6-cyclohexyl CH$_2$), 1.55(d,4-CH$_3$), 0.65 (d,2-CH$_3$)

$^{13}$C NMR (CDCl$_3$, 400 MHz) δ ppm: 20.2 (CH$_3$,2-cyclohexyl), 23.5 (CH$_3$,4-cyclohexyl), 30.1 (CH$_2$,6-cyclohexyl), 30.5 (CH$_2$,5-cyclohexyl), 34.2 ($\underline{C}$H—CH$_3$), 50.6 (CH,1-cyclohexyl), 121.0 (CH,3-pyridyl), 122.2 (CH,5-pyridyl), 127.5 ($\underline{C}$H=C—CH$_3$), 132.8 (q:CH=$\underline{C}$—CH$_3$), 136.0 (CH,4-pyridyl), 149.2 (CH,6-pyridyl), 165.5 (q,2-pyridyl)

2-[(1R,2S)-2,4-dimethylcyclohex-3-en-1-yl]pyridine (Kovats 1511)

$^1$H NMR (CDCl$_3$, 400 MHz) δ ppm: 8.40 (d,6-pyridyl), 7.42 (dd,4-pyridyl), 6.95 (d,3-pyridyl), 6.90 (dd,5-pyridyl), 5.31 (d,$\underline{C}$H=C—CH$_3$), 3.0 (ddd,1-cyclohexyl), 2.41 (m,2-cyclohexyl), 2.0-1.7 (m,5,6-cyclohexyl CH$_2$), 1.55 (d,4-CH$_3$), 0.40 (d,2-CH$_3$)

$^{13}$C NMR (CDCl$_3$, 400 MHz) δ ppm: 15.9 (CH$_3$,2-cyclohexyl), 21.5 (CH$_2$,6-cyclohexyl), 23.5 (CH$_3$,4-cyclohexyl), 30.5 (CH$_2$,5-cyclohexyl), 34.2 ($\underline{C}$H—CH$_3$), 45.2 (CH,1-cyclohexyl), 120.8 (CH,3-pyridyl), 121.8 (CH,5-pyridyl), 127.6 ($\underline{C}$H=C—CH$_3$), 132.8 (q:CH=$\underline{C}$—CH$_3$), 135.8 (CH,4-pyridyl), 148.9 (CH,6-pyridyl), 164.5 (q,2-pyridyl)

EXAMPLE 2

This example describes synthesis of 2-(2,4-dimethylcyclohexyl)pyridine.

2-[(1R,2S)-2,4-dimethylcyclohex-3-en-1-yl]pyridine (39.8 g, 0.21 mol) prepared as described in Example 1 above, was dissolved in ethanol (500 ml) and the solution transferred to a 1 litre Buchi autoclave. 5% Pd/C (5 g) was then added, and the reaction mixture hydrogenated at 5 bar hydrogen pressure while heating with an oil bath. There was almost no hydrogen uptake until the temperature reached 80° C., whereupon uptake was relatively rapid, and was complete within 2 hours. The reaction mixture was then sampled, and analysed by GLC and tlc. The results of GLC analysis are shown in the table below, whereby the reaction mixture was compared with the control odour standard identified herein as "Batch No. 5", a composition containing 2-[(1R,2R,4R)-2,4-dimethylcyclohexyl]pyridine (Kovats 1434, 20%) and 2-[(1R,2R,4S)-2,4-dimethylcyclohexyl]pyridine (Kovats 1454, 73%). The results are as follows:

| Batch No. 5 | Reaction Mixture |
| --- | --- |
| KOVATS 1434 20% | KOVATS 1422 40% |
| KOVATS 1454 73% | KOVATS 1435 11% |
|  | KOVATS 1453 12% |
|  | KOVATS 1499 11% |

Analysis of the reaction mixture by tlc (silica; hexane 90%:MTBE 10%) indicated only two products, with the less polar product corresponding to 2-[(1S,2R,4R)-2,4-dimethylcyclohexyl]pyridine. The reaction mixture was then cooled and the catalyst removed by filtration through a 1.5 cm bed of Celite. Ethanol was removed from the filtrate in vacuo and the residue purified by chromatography under the same conditions used for tlc analysis, to give a colourless oil (15.6 g) identified as 2-[(1S,2R,4R)-2,4-dimethylcyclohexyl]pyridine. Further elution gave a colourless oil (7.1 g, 14%) which was short-path distilled, b.p. 95° C./0.0 mbar. This material was compared to Batch No. 5 and was shown by GLC to be a mixture of isomers, 2-[(1R,2R,4S)-2,4-dimethylcyclohexyl]pyridine and 2-[(1R,2R,4R)-2,4-dimethylcyclohexyl]pyridine as shown below:

| Batch No. 5 | Purified Mixture |
|---|---|
| KOVATS 1434 20% | KOVATS 1435 36% |
| KOVATS 1454 73% | KOVATS 1453 60% |

2-[(1S,2R,4R)-2,4-dimethylcyclohexyl]pyridine

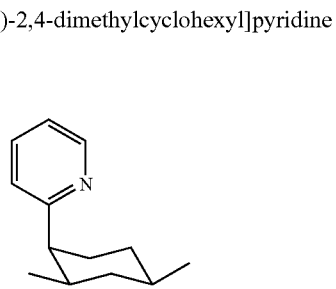

$^1$H NMR (CDCl$_3$, 400 MHz) δ ppm: 8.50 (d,6-pyridyl), 7.45 (dd,4-pyridyl), 7.10 (d,3-pyridyl), 7.00 (dd,5-pyridyl), 3.00 (ddd,1-cyclohexyl), 2.00-1.40 (m,cyclohexyl), 1.00 (d, CH$_3$), 0.74 (d, CH$_3$)

$^{13}$C NMR (CDCl$_3$, 400 MHz) δ ppm: 20.3 (CH$_3$), 23.0 (CH$_3$), 30.0 (CH$_2$), 31.6 (CH$_2$), 33.1 (CH—CH$_3$), 35.4 (CH—CH$_3$), 38.9 (CH$_2$), 46.6 (CH,1-cyclohexyl), 120.7 (CH,3-pyridyl), 124.2 (CH,5-pyridyl), 135.4 (CH,4-pyridyl), 148.7 (CH,6-pyridyl), 164.9 (CH,2-pyridyl)

2-[(1R,2R,4S)-2,4-dimethylcyclohexyl]pyridine

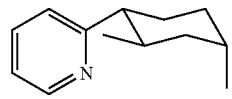

$^1$H NMR (CDCl$_3$, 400 MHz) δ ppm: 8.42 (d, 6-pyridyl), 7.43 (dd, 4-pyridyl), 7.05 (d, 3-pyridyl), 6.95 (dd, 5-pyridyl), 2.1 (ddd, 1-cyclohexyl), 2.15-1.20 (m, cyclohexyl), 1.05 (d, CH$_3$), 0.60 (d, CH$_3$)

$^{13}$C NMR (CDCl$_3$, 400 MHz) δ ppm: 18.4 (CH$_3$), 20.7 (CH$_3$), 27.7 (CH—CH$_3$ 30.3 (CH—CH$_3$), 31.8 (CH$_2$), 41.1 (CH$_2$), 54.5 (CH,1-cyclohexyl), 120.9 (CH,3-pyridyl), 122.2 (CH,5-pyridyl), 136.0 (CH,4-pyridyl), 149.2 (CH,6-pyridyl), 165.8 (CH,2-pyridyl)

EXAMPLE 3

This example describes the hydrogenation of 2-[(1R,2R)-2,4-dimethylcyclohex-3-en-1-yl]pyridine and compares the performance of the hydrogenation catalysts, Raney nickel and 5% palladium/carbon.

The reaction is as follows:

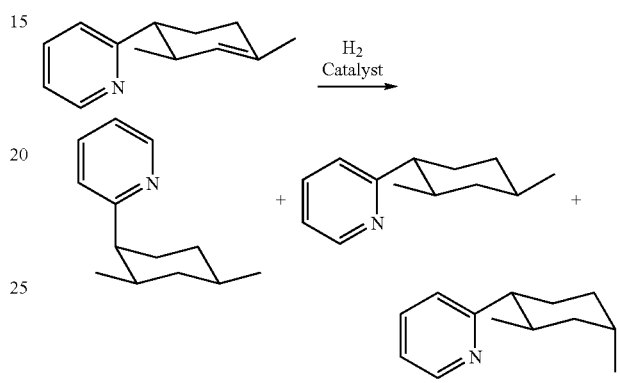

EXAMPLE 3A

2-[(1R,2R)-2,4-dimethylcyclohex-3-en-1-yl]pyridine (58 g, 0.31 mol) was dissolved in ethanol (500 ml) and Raney nickel (ex Fluka) (5 g) added. The reaction mixture was then hydrogenated in a Buchi autoclave at 5 bar of hydrogen pressure, while heating with an oil bath. There was little uptake of hydrogen until the temperature reached 80° C., whereupon uptake was rapid. The reaction mixture was sampled at 1 hour and two hours.

EXAMPLE 3B

In a separate experiment, 2-[(1R,2R)-2,4-dimethylcyclohex-3-en-1-yl]pyridine (58 g, 0.31 mol) was dissolved in ethanol (500 ml) and 5% Pd/C (6 g) added. The reaction mixture was then hydrogenated under the conditions described in Example 3A above.

The results of these experiments are indicated in the table below:

| KOVATS | 2-[(1R,2R)-2,4-dimethylcyclohex-3-en-1-yl]pyridine | Batch No. 5 | Example 3A Reaction Mixture (1 hour) | Example 3A Reaction Mixture (2 hours) | Example 3B |
|---|---|---|---|---|---|
| 1418 | | | 5% | 5% | 3% |
| 1433 | | 20% | 10% | 10% | 51% |
| 1452 | | 73% | 21% | 23% | 18% |
| 1466 | | | 3% | — | 7% |
| 1475 | | | 6% | 9% | 6% |
| 1484 | 82% | | 34% | 26% | — |

-continued

| KOVATS | 2-[(1R,2R)-2,4-dimethylcyclohex-3-en-1-yl]pyridine | Batch No. 5 | Example 3A Reaction Mixture (1 hour) | Example 3A Reaction Mixture (2 hours) | Example 3B |
|---|---|---|---|---|---|
| 1489 | 5% | | 4% | 6% | 2% |
| 1500 | 7% | | 8% | 10% | 3% |

The results show that for Example 3A, the ratio of desired isomers at Kovats 1433/1452 is very good, with the preferred isomer, 2-[(1R,2R,4S)-2,4-dimethylcyclohexyl]pyridine predominating. Under the same reaction conditions, but using the catalyst 5% palladium/carbon, the isomer ratios are reversed with the isomer at Kovats 1433 i.e. 2-[(1R,2R,4R)-2,4-dimethylcyclohexyl]pyridine being favoured.

EXAMPLE 4

This example describes the two-stage hydrogenation reaction of 2-[(1R,2R)-2,4-dimethylcyclohex-3-en-1-yl]pyridine in the presence of Raney nickel, followed by 5% palladium/carbon.

Stage 1

2-[(1R,2R)-2,4-dimethylcyclohex-3-en-1-yl]pyridine (60 g, 0.32 mol) was dissolved in ethonal (500 ml) and Raney nickel (ex Fluka) (5 g) added. The reaction mixture was hydrogenated in a Buchi autoclave at 5 bar hydrogen pressure, while heating on an oil bath. There was little uptake of hydrogen until the temperature reached 80° C., whereupon hydrogen uptake was rapid. The reaction mixture was sampled at 2 hours and the results compared with those obtained in Example 3A.

| KOVATS | 2-[(1R,2R)-2,4-dimethylcyclohex-3-en-1-yl]pyridine | Batch No. 5 | Example 3A Reaction Mixture (1 hour) | Example 3A Reaction Mixture (2 hours) | Sampled Reaction Mixture (2 hours) |
|---|---|---|---|---|---|
| 1418 | | | 5% | 5% | 4% |
| 1433 | | 20% | 10% | 10% | 9% |
| 1452 | | 73% | 21% | 23% | 28% |
| 1466 | | | 3% | — | 2% |
| 1475 | | | 6% | 9% | 9% |
| 1484 | 82% | | 34% | 26% | 26% |
| 1489 | 5% | | 4% | 6% | 7% |
| 1500 | 7% | | 8% | 10% | 10% |

Stage 2

The reaction mixture of stage 1 (60 g) was chromatographed on silica, using a mixture of hexane (90%) and MTBE (10%) as eluent.

Solvent was removed in vacuo from fractions 9 to 13 collected, giving a colourless oil (16.7 g) which was then short-path distilled to give 2-(2,4-dimethylcyclohexyl)pyridine as a colourless oil (1) (14.3 g) b.p. 90° C./0.0 mbar.

Fractions 14-33 collected were evaporated in vacuo to give a colourless oil (21.9 g) which still contained starting material. This oil was dissolved in ethanol (240 ml) and 5% Pd/C (2.5 g) added. The reaction mixture was then hydrogenated in a Buchi autoclave at 5 bar hydrogen pressure. External heating was supplied by an oil bath, there being little hydrogen uptake until the internal, reaction mixture temperature reached 80° C., whereupon uptake was then fairly rapid and complete within 2 hours. After cooling, the reaction mixture was filtered through Hyflo (HYFLO is a Trade Mark) to remove the catalyst, the filtrate evaporated in vacuo and the residue chromatographed (silica; hexane 90%:MTBE 10%) to give a colourless oil (16.2 g). This was then short-path distilled to give 2-(2,4-dimethylcyclohexyl)pyridine as a colourless oil (2) (13.8 g) b.p. 90° C./0.0 mbar.

Analysis of products (1) and (2) (47% yield in total) by GLC gave the following:

| (1) | KOVATS 1433 (21%) | KOVATS 1452 (73%) |
| (2) | KOVATS 1433 (45%) | KOVATS 1450 (54%) |

Both products contained high amounts of the desired isomer at Kovats 1450/2. The use of Raney nickel gives a good isomer ratio of 2-[(1R,2R,4S)-2,4-dimethylcyclohexyl]pyridine to 2-[(1R,2R,4R)-2,4-dimethylcyclohexyl]pyridine, but the reaction may overreduce before reaching completion, resulting in the production of a piperidine by-product. Stopping the reaction at this stage, e.g. before overreduction becomes too much of a problem, and then taking the reaction to completion using 5% Pd/C gives more favourable isomer ratios than when 5% Pd/C is simply used as the hydrogenation catalyst.

The invention claimed is:
1. A compound having the structure

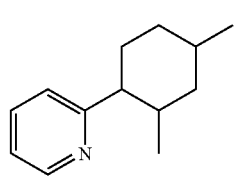

2. A compound according to claim 1, in the form of an individual isomer selected from (i) 2-[(1S,2R,4R)-2,4-dimethylcyclohexyl]pyridine;
(ii) 2-[(1R,2R,4R)-2,4-dimethylcyclohexyl]pyridine;
(iii) 2-[(1R,2R,4S)-2,4-dimethylcyclohexyl]pyridine;
(iv) 2-[(1S,2S,4S)-2,4-dimethylcyclohexyl]pyridine;
(v) 2-[(1S,2R,4S)-2,4-dimethylcyclohexyl]pyridine;
(vi) 2-[(1S,2S,4R)-2,4-dimethylcyclohexyl]pyridine;
(vii) 2-[(1R,2S,4S)-2,4-dimethylcyclohexyl]pyridine; and
(viii) 2-[(1R,2S,4R)-2,4-dimethylcyclohexyl]pyridine.

3. A compound according to claim 2, in the form of a mixture of two or more of the specified isomers.

4. A compound according to claim 3, in the form of a mixture of 2-[(1R,2R,4R)-2,4-dimethylcyclohexyl]pyridine and 2-[(1R,2R,4S)-2,4-dimethylcyclohexyl]pyridine.

5. A compound according to claim 4, wherein the mixture contains 2-[(1R,2R,4R)-2,4-dimethylcyclohexyl]pyridine in an amount of between 80% and 20% by weight of the total weight of the mixture, and 2-[(1R,2R,4S)-2,4-dimethylcyclo-hexyl]pyridine in an amount of between 20% and 80% by weight of the total weight of the mixture.

6. A compound according to claim 1, made by a Diels-Alder reaction between 2-vinylpyridine and 2-methyl-1,3-pentadiene to produce 2-(2,4-dimethylcyclohex-3-en-1-yl)pyridine, and subjecting 2-(2,4-dimethylcyclohex-3-en-1-yl)pyridine to a hydrogenation reaction.

7. A perfume comprising a compound in accordance with claim 1 in an olfactively effective amount.

8. A perfumed product comprising a compound in accordance with claim 1 or a perfume including such compound in an olfactively effective amount.

9. A method of making 2-(2,4-dimethylcyclohexyl)pyridine, comprising reacting 2-vinylpyridine and 2-methyl-1,3-pentadiene to cause a Diels-Alder reaction to produce 2-(2,4-dimethylchclohex-3-en-1-)pyridine, and subjecting 2-(2,4-dimethylcyclohex-3-en-1-yl)pyridine to a hydrogenation reaction to give 2-(2,4-dimethylcyclohexyl)pyridine.

10. A method of making a compound according to claim 4 or 5, comprising reacting 2-vinylpyridine and 2-methyl-1,3-pentadiene to cause a Diels-Alder reaction to produce a mixture of isomers of 2-(2,4-dimethylcyclohex-3-en-yl)pyridine, separating the isomer 2-[(1R,2R)-2,4-dimethylcyclohex-3-en-1-yl]pyridine from the mixture, and subjecting it to a hydrogenation reaction to give a mixture of isomers of 2-(2,4-dimethylcyclohexyl)pyridine, and isolating therefrom 2-[(1R,2R,4R)-2,4-dimethylcyclohexyl]pyridine and 2-[(1R,2R,4S)-2,4-dimethylcyclohexyl]pyridine as a mixture.

11. A method according to claim 10, wherein the hydrogenation reaction is carried out as a one stage process using Raney nickel as the hydrogenation catalyst.

12. A method according to claim 10, wherein the hydrogenation reaction is carried out as a two stage process.

13. A method according to claim 12, wherein the two stage hydrogenation reaction is carried out using Raney nickel for the first stage hydrogenation and palladium supported on carbon for the second stage hydrogenation.

* * * * *